(12) United States Patent
Simon

(10) Patent No.: US 9,138,352 B2
(45) Date of Patent: Sep. 22, 2015

(54) BLAST ATTENUATING EARPLUG

(71) Applicant: The John Hopkins University, Baltimore, MD (US)

(72) Inventor: Daniel H. Simon, Eldersburg, MD (US)

(73) Assignee: The Johns Hopkins University, Baltimore, MD (US)

( * ) Notice: Subject to any disclaimer, the term of this patent is extended or adjusted under 35 U.S.C. 154(b) by 231 days.

(21) Appl. No.: 13/713,402

(22) Filed: Dec. 13, 2012

(65) Prior Publication Data

US 2013/0152949 A1 Jun. 20, 2013

Related U.S. Application Data

(60) Provisional application No. 61/577,993, filed on Dec. 20, 2011.

(51) Int. Cl.
*A61F 11/08* (2006.01)

(52) U.S. Cl.
CPC ........... *A61F 11/08* (2013.01); *A61F 2011/085* (2013.01)

(58) Field of Classification Search
CPC ......... A61F 11/06; A61F 11/08; A61F 11/10; A61F 11/12; A61F 2011/085; F16K 31/08; F16K 31/084; F16K 13/04; F16K 13/06
USPC ................... 128/864–868; 137/70, 71, 517
See application file for complete search history.

(56) References Cited

U.S. PATENT DOCUMENTS

| | | | | |
|---|---|---|---|---|
| 1,311,774 A | * | 7/1919 | Ritter | 137/71 |
| 2,465,606 A | * | 3/1949 | Reynolds | 128/868 |
| 2,619,960 A | * | 12/1952 | Reynolds | 128/868 |
| 3,468,338 A | * | 9/1969 | Patterson | 137/517 |
| 3,603,309 A | | 9/1971 | Wesemann | |
| 3,640,306 A | * | 2/1972 | Vogt | 137/512.1 |
| 3,730,181 A | * | 5/1973 | Fling | 128/868 |
| 3,891,233 A | * | 6/1975 | Damon | 280/737 |
| RE28,560 E | * | 9/1975 | Fling | 128/868 |
| 4,353,364 A | | 10/1982 | Woods | |
| 5,280,806 A | * | 1/1994 | Glazebrook | 137/517 |
| 5,631,965 A | | 5/1997 | Chang et al. | |
| 6,148,821 A | | 11/2000 | Falco | |
| 7,319,399 B2 | | 1/2008 | Berg | |
| 7,512,243 B2 | | 3/2009 | Haussmann | |
| 7,697,706 B2 | * | 4/2010 | Doty | 381/328 |
| 2006/0045284 A1 | * | 3/2006 | Haussmann et al. | 381/72 |
| 2010/0300461 A1 | | 12/2010 | Gilder et al. | |
| 2011/0029041 A1 | | 2/2011 | Wiskerke | |
| 2011/0103605 A1 | | 5/2011 | Killion et al. | |
| 2011/0197899 A1 | | 8/2011 | Rogers et al. | |
| 2011/0235843 A1 | | 9/2011 | Keady et al. | |

* cited by examiner

*Primary Examiner* — Alireza Nia
*Assistant Examiner* — Raymond E Harris
(74) *Attorney, Agent, or Firm* — Noah J. Hayward

(57) ABSTRACT

An earplug includes a body, insertable into an ear canal, where the body defines a channel having at least two ends. The channel can house a movable structure configured to allow passage of sound around the movable structure in a rest position, and to block at least a portion of the channel in a deflected position. The movable structure moves from the rest position to the deflected position based on receiving, at one of the at least two ends of the channel, a pressure wave having at least a threshold amplitude pressure to block at least a portion of the pressure wave from reaching the other end of the channel.

14 Claims, 7 Drawing Sheets

BLAST ATTENUATING EARPLUG

CROSS-REFERENCE TO RELATED APPLICATION

This application claims priority to and the benefit of U.S. Provisional Application No. 61/577,993 filed on Dec. 20, 2011, the entire contents of which are hereby incorporated herein by reference.

TECHNICAL FIELD

Example embodiments generally relate to earplugs and, more particularly, to earplugs capable of attenuating high pressure sound waves.

BACKGROUND

Earplugs and other ear protection devices have been developed and constructed to protect human (or other animal) ears from damaging effects of loud noises, whether constant or sudden. Present mechanical earplug technology uses a variety of constructions, which may provide benefits in different high noise environments. Some constructions use a sound deadening material, such as foam, to block or lessen sounds entering the ear canal. Other constructions include acoustic filters, such as cavities, side branches, or other apertures for redirecting sound waves, or vibrating diaphragms for absorbing sound waves.

Some earplugs attenuate sounds based on acoustic frequency. This allows for discerning sounds of useful frequencies, such as those used in speech, while blocking sounds of potentially harmful frequencies. This, however, may prevent an individual using the earplug from hearing some useful sounds that may be out of the designated frequency range. Electronic earplugs exist as well for actively attenuating or amplifying sound. Such earplugs use microphones, electronic circuitry, speakers, and a power source, which add to the cost of the earplug and may require some maintenance to ensure operation via power source and/or circuitry.

BRIEF SUMMARY

Accordingly, example embodiments may allow attenuation of sound based at least in part on an amplitude pressure thereof. For example, an earplug can be constructed to allow passage of sounds less than a threshold amplitude pressure, while blocking pressure waves that achieve or exceed the threshold amplitude. The earplug can have a body that defines a channel having two ends that remain substantially open to allow transmission of soft sounds received at one end to the other end with little or no attenuation. The earplug can react to large amplitude pressure by closing or otherwise blocking at least a portion of the channel to mitigate passage of sound related to the large amplitude pressure.

In one example embodiment, the earplug fits within an ear canal, and can include a movable structure defined in the channel. The movable structure can be initially positioned within the channel to allow passage of sound. When a pressure wave of a threshold amplitude pressure is received at an end of the channel, the movable structure can move within the channel to block at least a portion thereof, preventing the wave from reaching the other end of the channel. Thus, for example, the movable structure can be larger than at least part of the channel to allow the blocking. In one example, when the pressure wave of the threshold amplitude pressure is reduced below the threshold or otherwise no longer received, the movable structure can be repositioned within the channel to allow passage of sound. In a specific example, the channel defines a larger cavity within which the movable structure is disposed. Thus, in this example, the movable structure can move within the cavity to block the channel or allow passage of sound.

BRIEF DESCRIPTION OF THE SEVERAL VIEWS OF THE DRAWING(S)

Having thus described example embodiments in general terms, reference will now be made to the accompanying drawings, which are not necessarily drawn to scale, and wherein:

DETAILED DESCRIPTION

Figure 1:
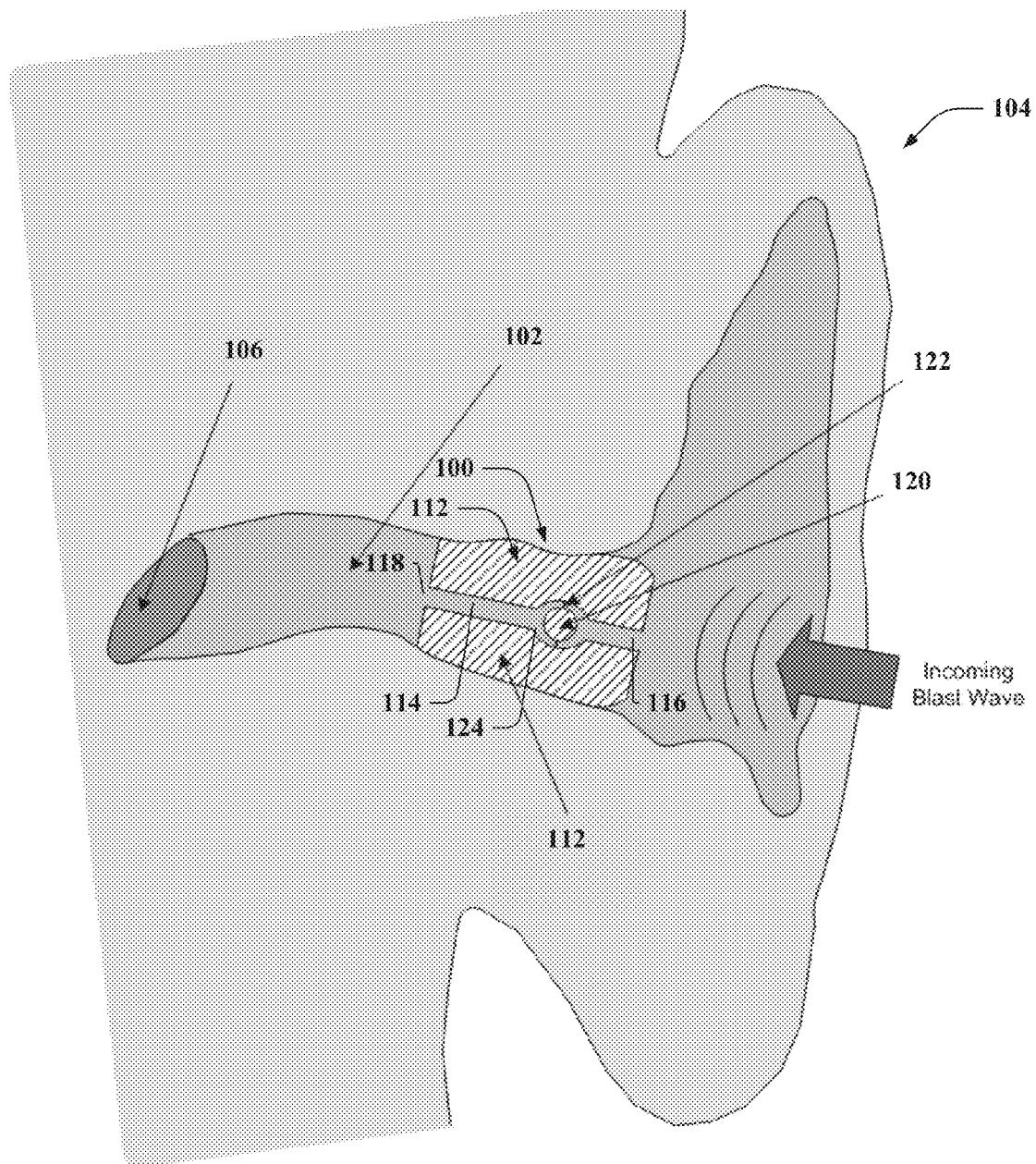
FIG. 1 is a cross section view of an earplug according to an example embodiment.

Various example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

Some example embodiments may enable attenuation of pressure waves having at least a threshold amplitude pressure, such as a blast or other sudden or constant loud noise. An earplug can be configured such that the pressure of the waves causes blocking in a channel that otherwise allows substantially unobstructed passage of the sound waves. The channel can have at least two ends for receiving sound at one end and allowing passing of the sound through the channel to the other end where the channel is not blocked. In one example, a movable structured is employed within the channel to cause the blocking. The movable structure can initially be disposed in a rest position within the channel, and receipt of a pressure wave above a threshold amplitude pressure can cause the movable structure to urge or move to a deflected position blocking the channel.

In a specific example, the movable structure is larger than a width of the channel at least at one location and is disposed in a cavity within the channel; the pressure wave above the threshold amplitude pressure causes the movable structure within the cavity to move toward the other end of the channel, which causes blocking of the channel where the channel has a width less than the size of the movable structure at that end. In one example, the earplug can be configured such to allow the movable structure to return to the rest position upon cessation or reduction of the amplitude pressure of the pressure wave, and in this example, the earplug can be designed for repeated use.

Figure 2:
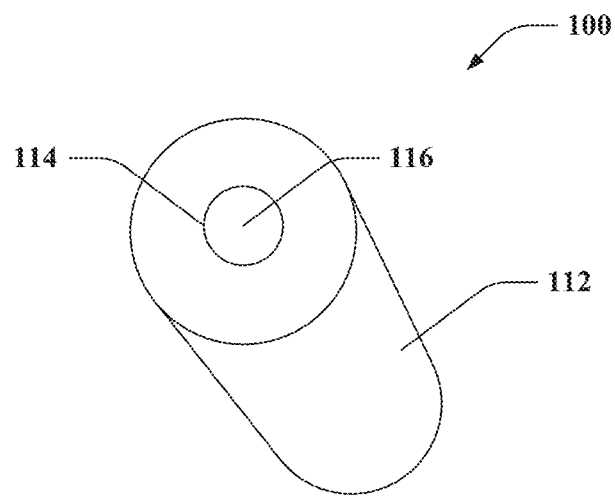
FIG. 2 is a three dimensional view of one end of an earplug according to an example embodiment.
Figure 3:
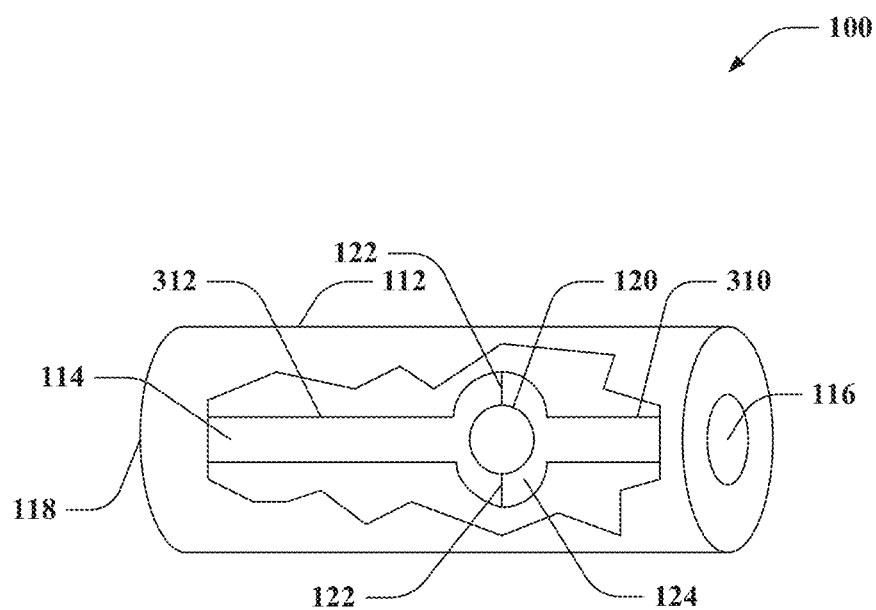
FIG. 3 is a cross section view of an earplug with inlet and outlet portions according to an example embodiment.
Figure 4A:
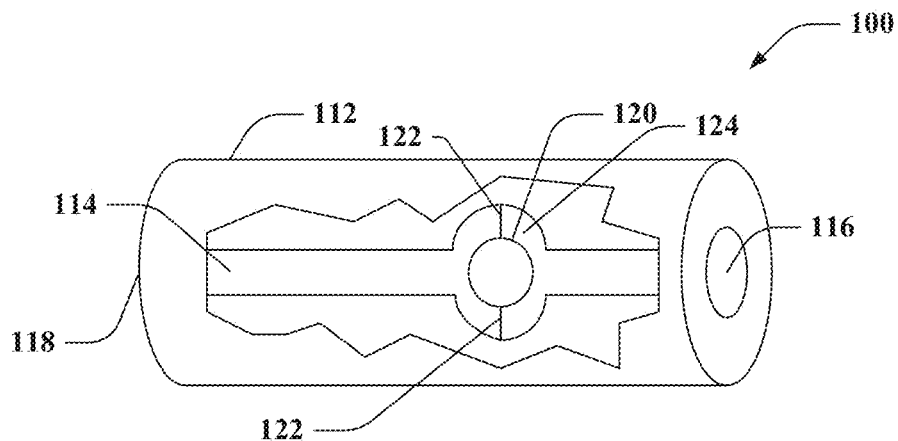
FIGS. 4A and 4B are cross section views of an earplug with a movable structure in a rest position according to example embodiments.
Figure 4B:
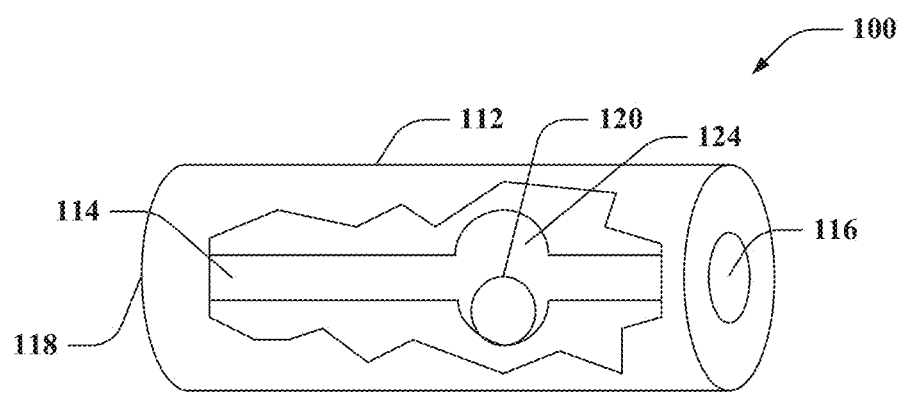
Figure 5A:
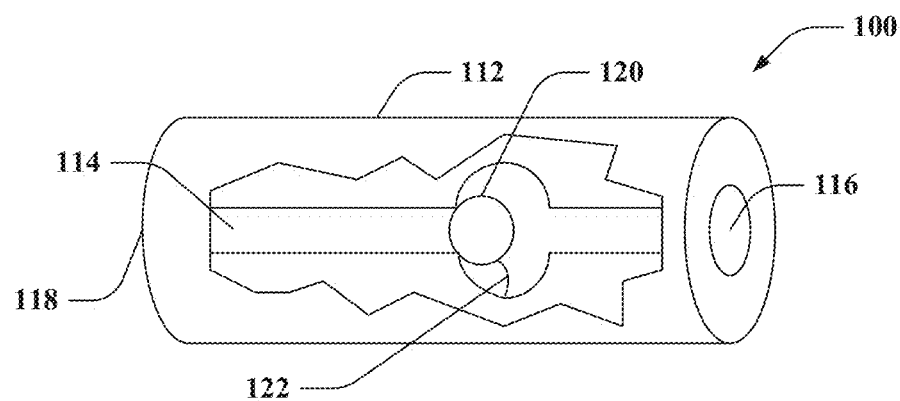
FIGS. 5A-5C are cross section views of an ea with a movable structure in a deflected position according to example embodiments.
Figure 5B:
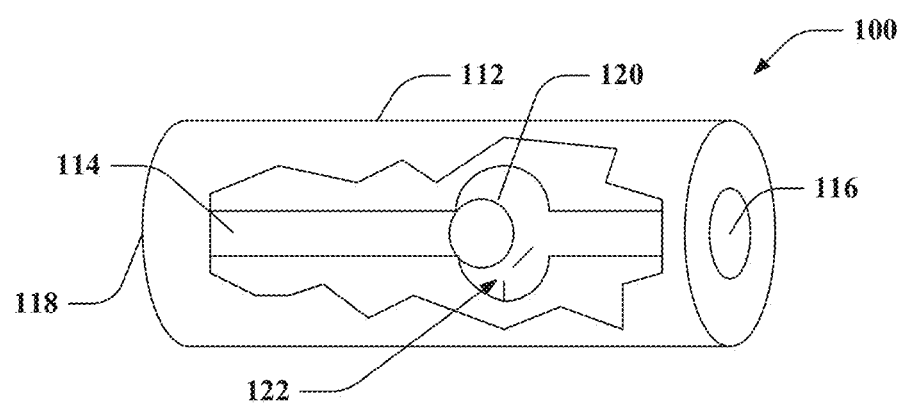
Figure 5C:
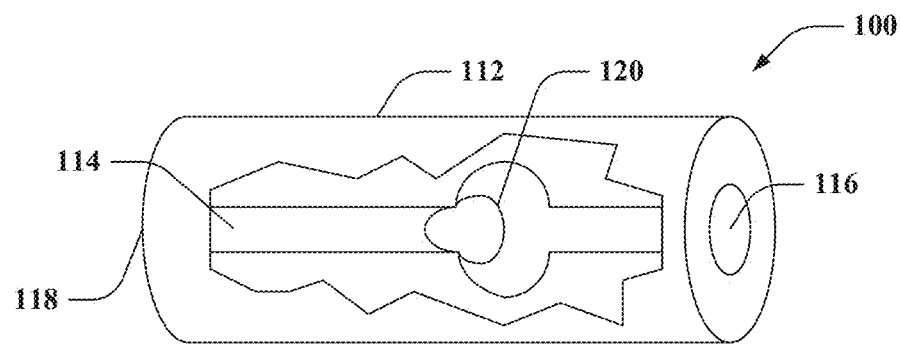
Figure 6A:
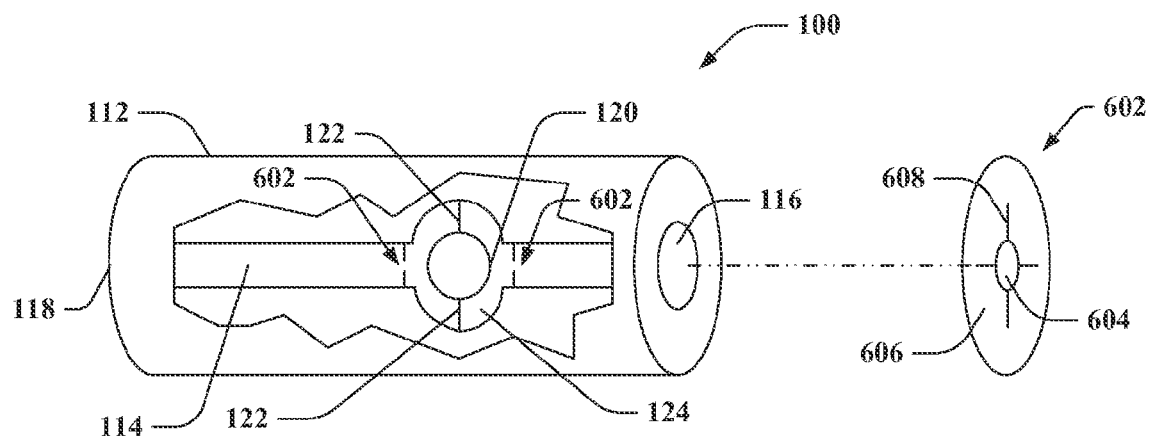
FIGS. 6A and 6B are cross section and three dimensional views of an earplug having one or more scored or otherwise intentionally weakened orifice plates situated near a movable structure.
Figure 6B:
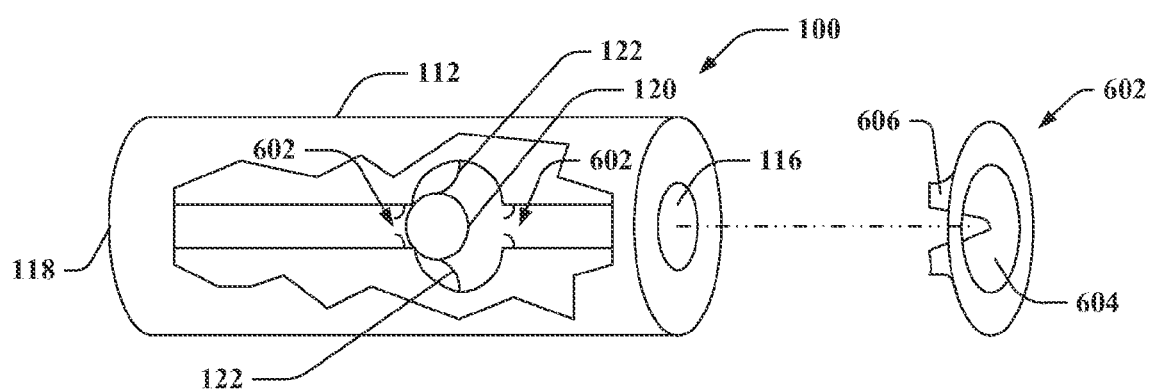
Figure 7:
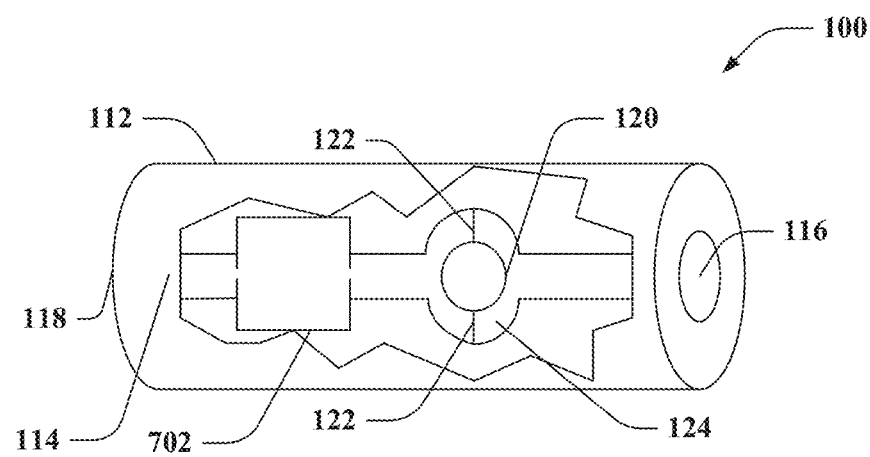
FIG. 7 is a cross section view of an earplug with an acoustic filter situated near a movable structure.

FIG. 1 is a cross section view of an earplug inserted into a human ear according to an example embodiment. FIG. 2 is a three dimensional view of an end of an example earplug. FIG. 3 is a cross section cut-away view of an example earplug defining an inlet and outlet portion in accordance with aspects described herein. FIGS. 4A and 4B are cross section cut-away views of example earplugs with movable structures in a rest position. FIGS. 5A, 5B, and 5C are cross section cut-away views of example earplugs with movable structures in a deflected position. FIGS. 6A and 6B are cross section cut-away views of example earplugs and three dimensional views of orifice plates installed therein. FIG. 7 is a cross section cut-away view of an example earplug with an additional acoustic filter. It should be appreciated that although the earplugs of FIGS. 1-7 show a substantially cylindrically shaped body, portions of the channel, diaphragms, etc., any suitable shape could be employed in connection with other example embodiments, as described further herein.

Referring now to FIG. 1, an example earplug 100 installed within an ear canal 102 of a human ear 104 is illustrated. The earplug 100 can function to protect the eardrum 106, or other portions of the inner ear, from consistent or sudden sounds having at least a threshold amplitude pressure, such as a blast or explosion, while allowing passage of sound waves that do not achieve the threshold amplitude pressure. The earplug 100 can include a body 112, which defines a channel 114. FIG. 1 shows a cross section view of the earplug 100, and thus the body 112 as depicted appears to have top and bottom portions that define the channel 114. While this can be one configuration, it is to be appreciated that the body 112 can also be of a complete cylindrical or other encompassing shape, as described further herein, where the channel 114 is defined completely within the body 112. Moreover, though the channel 114 is shown disposed as longitudinally centered and parallel to the body 112, the channel 114 can be alternatively longitudinally off-centered in the body 112 and/or unparallel to the body 112.

For example, the channel 114 can include at least two ends 116 and 118. The ends 116 and 118 can be substantially longitudinally opposed such that one end 116 can be located distally to the ear canal 102 (referred to herein as the distal end 116), while the other end 118 is located proximally to the ear canal 102 (referred to herein as the proximal end 116) when the earplug 100 is installed in an ear 104. For example, the distal end 116 can face an environment in which sound waves are received. Thus, sound received in the distal end 116 can pass through the channel 114 to the proximal end 118 and into the ear canal 102. The channel 114 additionally includes a movable structure 120 that can operate to block the channel 114 upon receiving pressure waves achieving a threshold amplitude pressure, thus providing attenuation of the pressure wave to prevent at least some of the pressure from passing through the channel 114 and into the ear canal 102. The movable structure 120 may be disposed within the channel 114 such that it is supported in a rest position within the channel 114 to initially allow passage of sound. The movable structure 120 may be movable to a deflected position to block at least a portion of the channel 114 to prevent or otherwise impede passage of pressure waves when the waves achieve the threshold amplitude pressure. For example, amplitude pressure from blast waves can cause a combination of pressure and drag forces on the movable structure 120, resulting in urging or movement of the movable structure 120 toward the proximal end 118 of the channel 114, such that a sufficiently strong blast wave can cause the movable structure 120 to contact the channel 114. In some examples, the threshold amplitude pressure of the pressure wave that causes movement of the movable structure 120 can be around 10 pounds per square inch (psi). In some cases, the threshold amplitude pressure supported by the functions of the earplug 100 described herein can be in the range of 10-75 psi.

Various configurations are described herein to illustrate examples of this functionality. It is to be appreciated that the described configurations are not an exhaustive list of those that achieve the desired functions, but examples of potential configurations. For example, the channel 114 may optionally include a retaining mechanism 122 on one or both (or more) sides of the movable structure 120 allowing the movable structure 120 to flex, deflect, or otherwise move toward the proximal end 118 of the channel 114 upon receiving pressure waves that achieve the threshold amplitude pressure. Moreover, in an example configuration, the movable structure 120 is disposed in a cavity 124 defined by the channel 114 to allow passage of sound and movement of the movable structure 120. In other example configurations, however, the channel 114 may be of a substantially conical or frustum (or frusto-conical) shape, and the movable structure 120 can move from an end with a larger size or circumference (e.g., at distal end 116) to an end having a smaller size or circumference (e.g., proximal end 118) upon receiving a pressure wave achieving the threshold amplitude pressure. In this configuration, a cavity 124 may not be needed to house the movable structure 120.

Thus, in some examples, the movable structure 120 is positioned within the channel 114 and movement is restricted by constrictions at ends 116 and 118, and the shape or size of the channel 114 and/or movable structure 120 can be different than those shown in examples herein. In such examples, the shape of the channel 114 can encourage the movable structure 120 to naturally rest in the channel 114 in a position to allow passage of sound when the sound waves are below the threshold amplitude pressure, and to move toward the proximal end 118 to block the channel 114 from passing pressure waves (e.g., blast waves) achieving the threshold amplitude pressure. Additionally, though shown as circular or spherical, it is to be appreciated that the movable structure 120 can also be of substantially any shape such that at least a portion of the movable structure 120 is larger than the channel 114 to allow the movable structure 120 to block the channel 114 in its deflected position.

The earplug 100 can be constructed of a material to allow the earplug 100 to fit snugly within the ear canal 102, and/or to allow for easy removal, while ensuring integrity of the channel 114 to allow movable structure 120 to move as described. Thus, for example, an exterior portion of the body 112 can be composed of a flexible material, such as a silicone rubber, a memory foam, etc., to facilitate insertion into the ear and/or ear canal 102 and also to form a seal against the ear canal 102. In one example, once the seal is formed against the ear canal 102, sound received at the ear 104 may pass through the channel 114 to reach the ear canal 102. An interior portion of the body 112 that defines the channel 114 (e.g., or the channel 114 itself) can be composed of a more rigid material, such as plastic, metals, composites, etc., to ensure the functionality described herein. In another example, however, the interior portion of the body 112 (e.g., or the channel 114 itself) can be composed of a flexible material as well, such that insertion of the earplug 100 into an ear canal 102 causes compression of the channel 114 for allowing the movable structure 120 to block the channel 114 in the deflected position.

The movable structure 120, though larger than the channel 114 in at least one portion such to allow blocking of the channel 114, has a mass sufficiently small to allow the movable structure 120 to move quickly enough to block the channel 114 before the pressure wave having at least the threshold amplitude pressure penetrates the proximal end 118. The movable structure 120 can thus be a solid structure composed of low density materials, such as expanded polystyrene, various aerogel formulations, a multilayer material, a composite material, etc. In one example, the movable structure 120 can be formed of a somewhat malleable material such that a portion of the movable structure 120 can partially lodge within the channel 114, thus sealing at least a portion of a sidewall of the channel 114, upon moving in the direction of the channel 114 in the deflected position. Moreover, in an example, the movable structure 120 can be composed of a porous or hollow material that provides some resistance to airflow. In an example, the material can be selected or otherwise formulated to withstand force of airflow caused by sound waves below the threshold amplitude pressure, while the force of airflow caused by a blast wave, or other pressure waves achieving the threshold amplitude pressure, can cause movement of the movable structure 120. Thus, receiving the blast wave can cause the movable structure 120 to move toward the proximal end 118 of the channel 114 blocking the channel 114.

In another example, where the retaining mechanism 122 is present, a material selected for composing the retaining mechanism 122 can facilitate movement of the movable structure 120 based on a force of airflow from pressure waves having the threshold amplitude pressure. Thus, in this example, the retaining mechanism 122 can be lightweight and compliant, such as a thin filament where the size and/or composition allows for flexing or breaking in response to the force from the sound waves of at least the threshold amplitude pressure, such that the movable structure 120 moves toward the proximal end 118 of the channel 114 upon receiving the pressure waves. The material for the retaining mechanism 122 can be selected based on properties of material used to formulate the movable structure 120 as well to provide a desired strength such that the movable structured 120 withstands force of sound waves below the threshold amplitude pressure, but moves upon force from pressure waves having at least the threshold amplitude pressure.

It is to be appreciated that the functionality described herein can be used in conjunction with other earplug technologies, such as passive acoustic filters, to attenuate other loud sounds. For example, the acoustic filters can include additional diaphragms, cavities, side branches, or other orifices in the channel 114. The added filters can be positioned or designed to disengage above threshold conditions so as not to interfere with the function of the movable structures 120. For example, diaphragms or orifice plates used in a supplemental sound filter can be designed to rupture in the event of a pressure wave of threshold amplitude pressure. In one example, the filters can be displaced on a portion of the channel closer to the proximal end 118 and/or the distal end 116. In any case, the earplug 100 can be a blast attenuating earplug 100 designed to protect from hearing damages. Such an earplug 100 can be used in a variety of applications, such as to protected soldiers and civilians from hearing damage due to explosive blasts (e.g., those caused by weapons or high pressure systems, such as compressed gases or energetic materials, explosives, propellants, fuels, etc.).

FIG. 2 illustrates a three dimensional view of an end of an example earplug 100 comprising a body 112 and a channel 114. The channel 114, as depicted, has an end 200, which can be the distal end 116 or the proximal end 118, as described, with a corresponding end located longitudinally adjacent to end 200. As shown, for example, the body 112 can completely surround the channel 114, in one example. Moreover, as described, it is to be appreciated that the body 112 and/or the channel 114 are not limited to cylindrical or circular shapes, but can be conical, frustum, quadrilateral, triangular, ear canal or other irregular shape, etc.

FIG. 3 illustrates across section view of an example earplug 100 including a body 112 defining a channel 114 with a distal end 116 and a proximal end 118, as described. In addition, a movable structure 120 is disposed within the channel 114 in a defined cavity 124 and attached to the channel 114 by one or more retaining mechanisms 122. The channel 114 also includes an inlet portion 310 between the distal end 116 and the cavity 124, and an outlet portion 312 between the proximal end 118 and the cavity 124. At a rest position, the movable structure 120 is situated within the cavity 124 and biased to a certain position to allow passage of sound from the distal end 116, through the inlet portion 310 of the channel 114, in the cavity 124, through the outlet portion 312 of the channel 114, and out the proximal end 118 (and into the ear canal 102). When a pressure wave achieving a threshold amplitude pressure is received in distal end 116, and passes through the inlet portion 310, the amplitude pressure can cause the movable structure 120 to move to a deflected position within the cavity 124 towards the outlet portion 312. In this regard, given enough force, the movable structure 120 can contact the outlet portion 312 of the channel 114 via the cavity 124, and can thus block the outlet portion 312, which can cause attenuation of the pressure wave.

Though shown and described herein with a single channel 114, it is to be appreciated that an earplug 100 may have multiple channels 114 (e.g., which can each house a movable structure 120). In another example, an earplug 100 may have a single inlet portion 310 with multiple outlet portions 312 and/or corresponding cavities 124, movable structures 120, etc.

FIG. 4A illustrates a cross section view of an example earplug 100 with a movable structure 120 in a rest position supported by one or more retaining mechanisms 122. The earplug 100 has a body 112 that defines a channel 114. A movable structure 120 is disposed within the channel 114 in a cavity 124 defined by the channel 114. In addition, retaining mechanisms 122 are shown that support the movable structure 120 in a rest position when pressure waves achieving a threshold amplitude pressure are not being received. The retaining mechanisms 122 can extend radially inwardly from a sidewall of the channel 114 (e.g., in the cavity 124) to support the movable structure 120. Though shown as connecting the movable structure 120 to two adjacent locations of the channel 114 in the cavity 124, it is to be appreciated that additional retaining mechanisms can be provided as well to attach the movable structure 120 to the channel 114 in the cavity 124 at the rest position. In one example, the retaining mechanism(s) 122 can be a beam that is attached to the channel 114 within the cavity 124 at two adjacent locations along the width or diameter of the cavity 124, and the movable structure 120 can be disposed on the beam.

In one example, each of the retaining mechanism(s) 122 can be a thin filament that flexes or breaks upon the movable structure 120 being moved by a three caused by a pressure wave having at least the threshold amplitude pressure. For example, the filament can be constructed with a thickness, size, or tensile strength sufficient to withstand force of the movable structure 120 being biased toward the proximal end 118 upon being subject to sound waves below the threshold amplitude pressure, while bending or breaking under force of the movable structure 120 subjected to a pressure wave achieving the threshold amplitude pressure, such as a blast wave. In another example, the retaining structure 120 can be a webbing type of material to which the movable structure 120 is attached to allow passage of sound waves through the webbing, where the webbing has a thickness, size, or tensile strength to withstand three of the movable structure 120 only until the movable structure 120 is impacted by a pressure wave having at least the threshold amplitude pressure, as described.

In another example, the retaining mechanism(s) 122 can form a cantilevered beam that extends from a sidewall of the channel 114 (or cavity 124), and allows the movable structure 120 to be displaced towards the proximal end 118 of the channel 114 upon experiencing force of a pressure wave having at least the threshold amplitude pressure. In either example, the movable structure 120 can be biased in the rest position by an opposing force (e.g., a magnetic, electrostatic, or similar force, strength of the retaining mechanism, etc.), and force caused by pressure waves of at least the threshold amplitude pressure can overcome the opposing force, resulting in movement of the movable structure 120 by the pressure wave to its deflected position, which can cause the retaining structure 120 to break, bend, or otherwise move, depending on the configuration of the retaining mechanism(s) 122. Where the retaining mechanism(s) 122 remain in tact once the movable structure 120 is moved by the pressure wave to the deflected position, and when the amplitude pressure reduces, the opposing force causing the rest position is no longer overcome, and the opposing force can move the movable structure 120 back to the rest position.

In a specific example, the movable structure 120 can include a magnet displaced on the top of the movable structure 120, and the top of cavity 124 can have a magnet of opposite polarity to attract the movable structure 120 to the top of the cavity 124, resulting in a substantially upright rest position for the movable structure 120. The rest position of the movable structure 120 is also a factor of a position, strength, shape, etc., of the retaining mechanism(s) 122 with respect to the cavity 124. Moreover, though shown at the center of the cavity 124 in the rest position, it is to be appreciated that the movable structure 120 can be at substantially any position within the cavity 124 when at rest so long as sound waves can pass around the movable structure 120 and toward the proximal end 118 of the channel 114.

FIG. 4B illustrates across section view of an example earplug 100 with a movable structure 120 in a rest position without a retaining mechanism 122. The earplug 100 has a body 112 that defines a channel 114. A movable structure 120 is disposed within a channel 114 in a cavity 124 defined by the channel 114. The movable structure 120 is shown in a rest position. Thus, a retaining mechanism 122 may not be needed, and gravity can cause the movable structure 120 to rest at the bottom of the cavity 124. It is appreciated that other forces can be used to secure the movable structure 120 to contact a location in the cavity 124 (e.g., top, bottom, or substantially any location) in a rest position e.g., magnetic, electrostatic, or similar forces) where no retaining mechanism 122 is used. In another example, an adhesive can be used to secure the movable structure 120 to the location contacting the cavity 124 in the rest position. In any case, the force can have a strength required to hold the movable structure 120 until a pressure wave having the threshold amplitude pressure causes the movable structure 120 to move towards its deflected position with a sufficient counter acting force to move the movable structure 120. Once the pressure wave ceases or reduces in amplitude pressure, the force securing the movable structure 120 in the rest position, whether gravity, magnetic, electrostatic, etc., can cause the movable structure 120 to move back to rest position.

FIG. 5A illustrates a cross section view of an example earplug 100 with a movable structure 120 in a deflected position supported by a retaining mechanism 122. The earplug 100 has a body 112 that defines a channel 114. A movable structure 120 is disposed within the channel 114 in a cavity 124 defined by the channel 114. In addition, a retaining mechanism 122 is shown that supports the movable structure 120 in a deflected position when sound waves achieving a threshold amplitude pressure are received. The retaining mechanism 122 bends or flexes, in this example, under a force caused by a pressure wave having at least the threshold amplitude pressure received at the distal end 116 of the channel 114 that deflects the movable structure 120 to the proximal end 118 of the channel 114. In one example, once the pressure waves cease or otherwise reduce in amplitude pressure, the force caused thereby lessens, and a counter acting force (e.g., the strength of the retaining mechanism 122, a magnetic, electrostatic, or similar force, etc. that holds the movable structure 120 in a rest position), as described, can move the movable structure 120 back to its rest position, as in FIG. 4A. In addition, as described, it is to be appreciated that additional retaining mechanisms 122 can be used as well and can similarly support movable structure 120.

FIG. 5B illustrates across section view of an example earplug 100 with a movable structure 120 in a deflected position. The earplug 100 has a body 112 that defines a channel 114. A movable structure 120 is disposed within the channel 114 in a cavity 124 defined by the channel 114. In addition, a retaining mechanism 122 is shown that supports the movable structure 120 in the rest position (e.g., as in FIG. 3), but snaps when pressure waves achieving a threshold amplitude pressure received at the distal end 116 of the channel 114 deflect the movable structure 120 toward the proximal end 118 of the channel 114. In one example, this earplug 100 may be single-use. In addition, as described, it is to be appreciated that additional retaining mechanisms 122 can be used as well and can similarly snap upon deflection of movable structure 120.

FIG. 5C illustrates a cross section view of another example earplug 100 with a movable structure 120 in a deflected position. This earplug 100 may be single-use as well. In particular, the movable structure 120, whether initially supported by a retaining mechanism 122 or not, is made of a more flexible or malleable material. In this example, when the movable structure 120 is deflected toward the proximal end 118 of the channel 114, the movable structure 120 can contact the channel 114 with such force caused by the pressure wave having at least the threshold amplitude pressure that at least a portion of the movable structure 120 enters the channel 114 and/or lodges or seals around at least a portion of the channel 114. The movable structure 120 can at least partially form the shape of the channel 114 due to the force. The movable structure 120 can be composed of materials, as described, such that the formation into the shape of the channel 114 is reversible or irreversible. In the former case, the earplug 100 may be constructed for repeated use.

FIGS. 6A and 6B illustrate a cross section view of an example earplug 100 with a movable structure 120 in a rest position supported by retaining mechanisms 122, as well as integrated components for attenuating lower intensity sound waves. The earplug includes several example membranes 602 employed within the earplug 100. The earplug 100 has a body 112 that defines a channel 114 extending between a proximal end 116 and a distal end 118. A movable structure 120 is disposed within the channel 114 in a cavity 124 defined by the channel 114. In addition, retaining mechanisms 122 are shown that support the movable structure 120 in a rest position when pressure waves achieving a threshold amplitude pressure are not being received, as shown in FIG. 6A. It is to be appreciated that a single retaining mechanism 122, additional retaining mechanisms, or no retaining mechanism may be used, as described in various examples herein. Moreover, retaining mechanism 122 may extend through movable structure 120, as described. One or more membranes 602 can be employed in the channel 114 to facilitate sound attenuation at pressures below the threshold pressure that causes the movable structure 120 to move.

In the depicted example, a membrane 602 is installed between the cavity 124 and the proximal end 116 of the channel 114, and another membrane 602 between the cavity 124 and the distal end 118 of the channel 114. It is to be appreciated that any number of membranes may be installed in the channel 114. The membranes may be flexible or rigid. The membranes may be solid or may include an orifice 604. The membranes 602 may provide sound filtering in a manner understood to one skilled in the art of acoustic engineering (e.g. by destructive interference of incoming sound waves). In addition, the membranes 602 may assist the earplug 100 in attenuating pressure waves of a threshold amplitude pressure. For example, the membranes 602 may control the rate of change of pressure on either side of the movable structure 120.

According to the example, membranes 602 may include slots 608 that separate the membrane into multiple flaps 606. Alternatively, membranes 602 may be scored along regions 608. These weakened regions can be configured to fracture at a pressure lower than an unaltered membrane. When a pressure wave of a threshold amplitude pressure is encountered, the membranes 602 may stretch or rupture. FIG. 6B illustrates an example earplug where the membranes 602 have deflected following a pressure wave of a threshold amplitude pressure. The resulting deflection of the membranes can facilitate movement of the movable structure 120 by subjecting the structure 120 to a faster rise in pressure on its upstream face. The threshold pressure that causes the membranes 602 to deflect may or may not be the same pressure that causes the movable structure 120 to move. The membranes 602 may or may not return to their original shape after the pressure wave has ceased. The membranes 602 may be designed for single use or repeated use.

FIG. 7 illustrates a cross section view of an example earplug 100 with a movable structure 120 in a rest position supported by retaining mechanism(s) 122, as well as an example acoustic filter 702 employed within the earplug 100. The earplug 100 has a body 112 that defines a channel 114 extending between a proximal end 116 and a distal end 118. A movable structure 120 is disposed within the channel 114 in a cavity 124 defined by the channel 114. In addition, retaining mechanisms 122 are shown that support the movable structure 120 in a rest position when pressure waves achieving a threshold amplitude pressure are not being received. It is to be appreciated that a single retaining mechanism 122, additional retaining mechanisms, or no retaining mechanism may be used in this example, as described in various examples herein. Moreover, retaining mechanism 122 may extend through movable structure 120, as described. In contrast to the example illustrated in FIGS. 6A and 6B, the acoustic filter 702 is in series with the cavity 124 rather than an integrated structure within channel 114, as one example configuration.

The acoustic filter 702 consists of a cavity with orifices at one or both ends. In the example illustrated in FIG. 7, the acoustic filter is shown at the distal end 118 of the channel 114. The acoustic filter may attenuate lower intensity sounds than that to which the movable structure 120 reacts. The acoustic filter 702 can provide sound filtering in a manner understood to one skilled in the art of acoustic engineering (e.g. by destructive interference of incoming sound waves). The acoustic filter 702 may also assist the device in attenuating pressure waves of a threshold amplitude pressure. For example, membranes 602 can be used to control the rate of change of pressure on either side of the movable structure. Though shown and described as being at the distal end 118 of the channel 114, it is to be appreciated that the acoustic filter 702 could also be at the proximal end 116, and/or multiple acoustic filters 702 can be employed in the channel 114. It is also appreciated that the orifice plates on either end of the acoustic filter 702 may behave like the membranes 602 illustrated in FIGS. 6A and 6B. For example, the orifice plates may rupture or deflect when exposed to a pressure wave of a threshold amplitude pressure.

Though shown and described as deflecting toward the proximal end 118 of the channel 114 in FIGS. 1-7 above, it is to be appreciated that the movable structure 120 can flex or otherwise be caused to move toward the distal end 116 of the channel 114. In one example, when a blast event occurs, following the initial force caused by the pressure wave, the air pressure can drop below ambient conditions for a period of time. Thus, where movable structure 120 moves to the proximal end 118 of the channel 114 based on the initial blast, and is not lodged in the channel 114, this rarefaction portion of the blast may cause the movable structure 120 to move toward and block the distal end 116 of the channel 114 in another deflected position, preventing rapid evacuation of air from the ear canal 102.

Many modifications and other embodiments of those non-limiting example embodiments set forth herein will come to mind to one skilled in the art to which these embodiments pertain having the benefit of the teachings presented in the foregoing descriptions and the associated drawings. Therefore, it is to be understood that the embodiments described herein are not to be limited to the specifics disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. An earplug comprising:
 a body configured to be inserted into an ear canal, the body defining a channel having at least two ends and a cavity;
 a movable structure disposed within the cavity in the channel; and a retaining mechanism comprising one or more filaments configured to retain the movable structure in a rest position within the cavity;

wherein the movable structure is configured to allow passage of sound around the movable structure in the rest position within the channel, block at least a portion of the channel in a deflected position within the channel, and move from the rest position to the deflected position based on receiving, at one of the at least two ends of the channel, a pressure wave having at least a threshold amplitude pressure, and wherein the retaining mechanism is configured to break responsive to the deflection of the movable structure to the deflected position.

2. The earplug of claim 1, wherein the body comprises an exterior portion and an interior portion, wherein the interior portion defines the channel.

3. The earplug of claim 2, wherein the exterior portion is composed of a flexible material, and the interior portion is composed of a rigid material.

4. The earplug of claim 3, wherein the flexible material comprises a silicon rubber or a memory foam.

5. The earplug of claim 1, wherein the channel comprises an inlet portion and an outlet portion, and wherein the movable structure is disposed between the inlet portion and the outlet portion.

6. The earplug of claim 5, wherein the movable structure contacts the outlet portion when in the deflected position.

7. The earplug of claim 6, wherein the movable structure contacts the outlet portion such to block the pressure wave having at least at the threshold amplitude pressure from reaching the outlet portion.

8. The earplug of claim 1, wherein the retaining mechanism comprises a cantilevered beam extending radially inward from a sidewall of the channel.

9. The earplug of claim 1, wherein a size of the movable structure is larger than a width of the channel.

10. The earplug of claim 1, wherein the movable structure is composed of expanded polystyrene, an aerogel formulation, a multilayer material, or a composite material.

11. The earplug of claim 1, wherein the movable structure is substantially hollow or porous.

12. The earplug of claim 1, wherein the at least two ends are disposed at opposite longitudinal ends of the body, the channel comprises one or more passive acoustic fitters configured to deform upon receiving pressure waves having at least another threshold amplitude pressure, and the one or more passive acoustic filters include one or more membranes or orifice plates.

13. The earplug of claim 1, wherein the threshold amplitude pressure is 10 pounds per square inch (psi).

14. The earplug of claim 1, wherein the threshold amplitude pressure is 10 to 75 pounds per square inch (psi).

* * * * *